(12) United States Patent
Miyachi et al.

(10) Patent No.: US 8,486,896 B2
(45) Date of Patent: Jul. 16, 2013

(54) LIPID TRIPEPTIDE-BASED HYDROGELATOR AND HYDROGEL

(75) Inventors: Nobuhide Miyachi, Chiyoda-ku (JP); Takehisa Iwama, Funabashi (JP); Masahiro Gotoh, Fukuoka (JP); Tatsuo Maruyama, Fukuoka (JP); Daisuke Koda, Fukuoka (JP)

(73) Assignees: Nissan Chemical Industries, Ltd., Tokyo (JP); Kyushu University, Fukuoka-Shi (JP)

( * ) Notice: Subject to any disclaimer, the term of this patent is extended or adjusted under 35 U.S.C. 154(b) by 470 days.

(21) Appl. No.: 12/452,472
(22) PCT Filed: Jul. 4, 2008
(86) PCT No.: PCT/JP2008/062214
§ 371 (c)(1), (2), (4) Date: May 6, 2010
(87) PCT Pub. No.: WO2009/005152
PCT Pub. Date: Jan. 8, 2009

(65) Prior Publication Data
US 2010/0279955 A1 Nov. 4, 2010

(30) Foreign Application Priority Data
Jul. 5, 2007 (JP) ................................. 2007-177539

(51) Int. Cl.
 C11D 3/32 (2006.01)
 D06P 1/00 (2006.01)
 C12N 1/04 (2006.01)
 C12N 9/00 (2006.01)
 C05F 11/00 (2006.01)
 C09K 3/00 (2006.01)

(52) U.S. Cl.
 USPC ......... 514/20.7; 514/21.9; 530/331; 426/573; 510/161; 510/403; 8/636; 435/260; 435/183; 71/27; 252/182.12

(58) Field of Classification Search
None
See application file for complete search history.

(56) References Cited

U.S. PATENT DOCUMENTS 7,863,417 B2 * 1/2011 Ziegler et al. ................. 530/331
(Continued)

FOREIGN PATENT DOCUMENTS

FR 2 877 221 A1 5/2006
(Continued)

OTHER PUBLICATIONS

Gilead et al., Self Organization of short peptide fragments:From Amyloid Fibrils to Nanoscale Supramolecular Assemblies, Supramolecular Chemistry. vol. 17 (1-2), p. 87-92, 2005.*
(Continued)

Primary Examiner — Robert A Wax
Assistant Examiner — Danah Al-Awadi
(74) Attorney, Agent, or Firm — Oliff & Berridge, PLC

(57) ABSTRACT

There is provided a hydrogelator that is capable of forming a hydrogel with an extremely small amount thereof over a liquid property range from acidic to alkaline, and a hydrogel having high environmental suitability, biocompatibility and biodegradability. A hydrogelator comprising a lipid peptide represented by Formula (1):

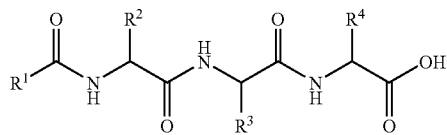

(where $R^1$ represents an aliphatic group having 9 to 21 carbon atoms; $R^2$, $R^3$ and $R^4$ independently represent a hydrogen atom, an alkyl group having 1 to 4 carbon atom(s) which may have a branched chain having 1 or 2 carbon atom(s), a phenylmethyl group or a —$(CH_2)_n$—X group, and at least one of $R^2$, $R^3$ and $R^4$ represents a —$(CH_2)_n$—X group; n represents the number of 1 to 4; X represents an amino group, a guanidino group, a —$CONH_2$ group or a 5-membered ring, a 6-membered ring or a fused heterocyclic ring composed of a 5-membered ring and a 6-membered ring which may have 1 to 3 nitrogen atom(s)) or a salt thereof, and a hydrogel comprising the hydrogelator.

8 Claims, 1 Drawing Sheet

U.S. PATENT DOCUMENTS

| | | | |
|---|---|---|---|
| 2004/0132667 A1* | 7/2004 | Lintner | 514/18 |
| 2007/0048245 A1 | 3/2007 | Belfer | |
| 2007/0099842 A1 | 5/2007 | Ziegler et al. | |

FOREIGN PATENT DOCUMENTS

| | | |
|---|---|---|
| JP | A 10-511340 | 11/1998 |
| JP | A 2002-085957 | 3/2002 |
| JP | A 2007-327949 | 11/2003 |
| JP | A 2004-250797 | 9/2004 |
| JP | A 2004-325505 | 11/2004 |
| JP | A 2007-501265 | 1/2007 |
| JP | A 2007-510791 | 4/2007 |
| JP | A 2007-515381 | 6/2007 |
| WO | WO 2004/099237 A1 | 11/2004 |
| WO | WO 2006/076042 A2 | 7/2006 |

OTHER PUBLICATIONS

European Search Report issued in European Patent Application No. 08790895.0 dated Jul. 26, 2010.

Van Bommel et al., "Responsive Cyclohexane-Based Low-Molecular-Weight Hydrogelators with Modular Architecture," Angew. Chem. Int. Ed., vol. 43, 2004, pp. 1663-1667.

Hartgerink et al., "Self-Assembly and Mineralization of Peptide-Amphiphile Nanofibers," Science, vol. 294, Nov. 23, 2001, pp. 1684-1688.

Petka et al., "Reversible Hydrogels from Self-Assembling Artificial Proteins," Science, vol. 281, Jul. 17, 1998, pp. 389-392.

Aggeli et al., "Self-Assembling Peptide Polyelectrolyte β-Sheet Complexes Form Nematic Hydrogels," Angew. Chem. Int. Ed., 2003, vol. 42, pp. 5603-5606.

Matsumoto et al., "The Supramolecular Hydrogel toward 'The Smart Biomaterials'," Dojin News, No. 118, 2006, pp. 1-16. (with English-language abstract).

International Search Report issued in corresponding International Patent Application No. PCT/JP2008/062214, mailed Aug. 19, 2008. (with English-language translation).

Written Opinion of the International Searching Authority issued in corresponding International Patent Application No. PCT/JP2008/062214, mailed Aug. 19, 2008. (with English-language translation).

Feb. 29, 2012 Office Action cited in Chinese Patent Application No. 200880023505.2 (with English Translation).

* cited by examiner

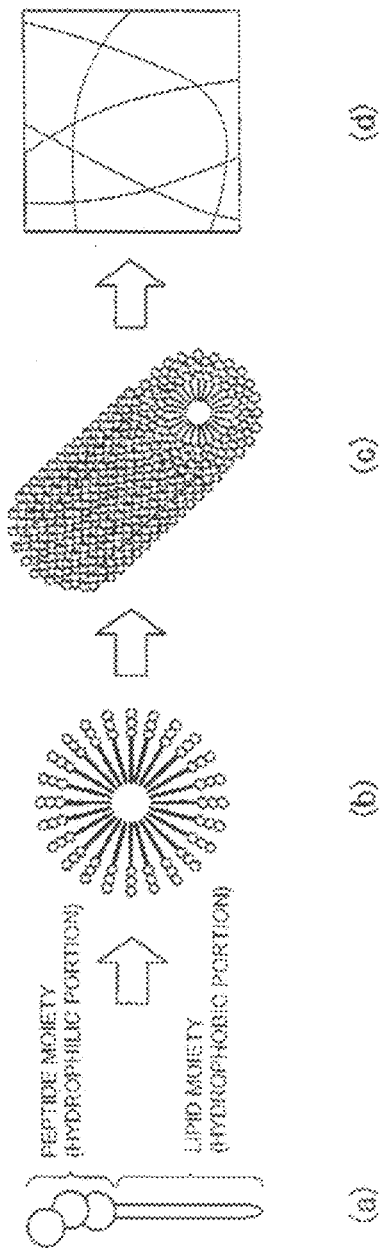

LIPID TRIPEPTIDE-BASED HYDROGELATOR AND HYDROGEL

TECHNICAL FIELD

The present invention relates to a novel lipid peptide-type hydrogelator, a fiber formed by the self-assembly of the hydrogelator and a hydrogel composed of the hydrogelator or the fiber and an aqueous solution or an alcohol aqueous solution.

The hydrogelator of the present invention can be suitably utilized in the production of various gel form base materials such as cosmetics, gel form foods such as agars and pharmaceutical preparations. In addition, a hydrogel obtained from the hydrogelator is preferred for various functional materials, for example, applications for products for daily use, such as cosmetics, (soft) contact lenses, paper diapers and aromatics; dry-land agricultural applications; chemical analysis applications such as chromatography; medicine/pharmacy applications; and bio-chemistry field applications such as carriers of protein, cell culture-related base materials and a bioreactor.

BACKGROUND ART

The hydrogel contains water as the medium, so that it is useful as a gel having high biocompatibility and is used in various fields such as applications for products for daily use, such as paper diapers, cosmetics and aromatics.

Examples of a related-art hydrogel include natural polymer gels such as agarose, and synthetic polymer gels in which between polymer chains is crosslinked through a chemical covalent bond such as an acrylamide gel.

Recently, functional gels in which various functions such as material retention capacities, an external stimulus responsive performance and a biodegradability in consideration of the environment are imparted to a hydrogel, have been attracting much attention, and there are performed attempts for developing various functions by introducing functional molecules into the natural or the synthetic polymer gels using a copolymerization reaction or the like.

Thus, for imparting new functions to a hydrogel, there is necessity for studying the nanostructure and the surface structure of the gel in detail. However, in the above method for introducing functional molecules using a copolymerization reaction, there are such various problems as problems in which the introduction rate of functional groups is limited and a precise molecule design is difficult, a problem of the safety of unreacted-remained materials, and a problem in which the preparation of the gel is extremely cumbersome.

As opposed to such a related-art "top-down type" development of functional materials, "bottom-up type" study for creating functional materials has been attracting much attention in which atoms or molecules which are the minimum units of the substance are assembled and new functions are discovered in the resultant assembly which is a supramolecule.

Also in the field of the gel, the development of a novel gel formed from a non-covalent gel fiber (so-called "supramolecule polymer") produced by the self-assembly of a low molecular weight compound has been progressed. This "self-assembly" refers to such a phenomenon that in a substance (molecule) group in a random state at first, molecules associate spontaneously by an intermolecular non-covalent interaction or the like under an appropriate external condition to grow to a macro functional assembly.

New gel attracts much attention because the control of the macroscopic structure or function of the gel is theoretically possible by controlling an intermolecular interaction or a weak non-covalent bond of a molecule assembly according to a molecule design of a monomer.

However, with respect to how the intermolecular interaction and non-covalent bond between low molecular weight compounds are controlled, there is not yet found an apparent methodology. In addition, in the study of the non-covalent gel, because the gel formation is relatively easy, the study of a self-assembly utilizing a hydrogen bond in an organic solvent is preceded and a self-assembled compound (that is, such as a hydrogelator) in an aqueous solution remains within a region of accidental findings.

Hydrogelators for forming a non-covalent gel which have been reported until now are broadly divided into the following three categories.

(1. Hydrogelators Having an Amphipathic Low Molecular Weight Molecule as the Skeleton Thereof)

This hydrogelator is created with an artificial lipid layer as a model and examples of the agent include surfactant-type gel-forming agents having a quaternary ammonium salt moiety as a hydrophilic portion and having an alkyl long chain as a hydrophobic portion, and ampholytic surfactant-type gel-forming agents in which hydrophilic portions of two surfactant-type molecules are coupled.

As one example of the hydrogel formed by such gel-forming agents, there is disclosed a molecule organizational hydrogel formed by adding an anion having a molecular mass of 90 or more to a dispersion aqueous solution of a cationic amphipathic compound having a branched alkyl group in the hydrophobic portion thereof (Patent Document 1).

(2. Hydrogelators Having a Skeleton in the Motif of Intravital Components)

Examples of this type of hydrogelators include gel-forming agents utilizing an association between molecule-assemblies through a peptide secondary structure skeleton (such as α-helix structure and β-sheet structure).

For example, there are disclosed a gel-forming agent having an α-helix structure (Non-patent Document 1) and a gel-forming agent having a β-sheet structure (Non-patent Document 2).

(3. Hydrogelators Having a Semi-Artificial Low Molecular Weight Molecule as the Skeleton Thereof)

This type of hydrogelators is composed of a combination of intravital components (hydrophilic portion) such as DNA bases, peptide chains and sugar chains and alkyl chains (hydrophobic portion) and the like and can be referred to as a gel-forming agent combining characteristics of the above two types of gel-forming agents. Here, the DNA base, the peptide chain and the sugar chain assume not only a role of enhancing the hydrophilicity, but also a role of imparting an intermolecular interaction such as a hydrogen bond.

For example, there are disclosed a hydrogelator containing a glycoside amino acid derivative having a sugar structure site having an N-acetylated glycoside structure of a monosaccharide or disaccharide (Patent Document 2) and disclosed a fine hollow fiber formed having a self-assembling property from a peptide lipid represented by General Formula: $RCO(NHCH_2CO)_mOH$ and a transition metal (Patent Document 3).

In addition, it is disclosed that an amphipathic peptide having a structure of (hydrophobic portion-cysteine residue (forming a disulfide bond during the network formation)-glycerin residue (imparting flexibility)-phosphorylated serin residue-cell adhesive peptide) forms a β-sheet type fiber network with a nuclear of the hydrophobic portion (Non-patent Document 3).

In addition, there is also disclosed a case where a sugar lipid-type supramolecule hydrogel was produced using a chemical library (Non-patent Document 4).

[Patent Document 1]
Japanese Patent Application Publication No. JP-A-2002-085957
[Patent Document 2]
Japanese Patent Application Publication No. JP-A-2003-327949
[Patent Document 3]
Japanese Patent Application Publication No. JP-A-2004-250797
[Non-Patent Document 1]
W. A. Pekata et al., SCIENCE, vol. 281, p. 389 (1998)
[Non-Patent Document 2]
A. Aggeli et al., Angew. Chem. Int. Ed., vol. 42, p. 5603 to 5606 (2003)
[Non-Patent Document 3]
Jeffrey D. Hartgerink, Elia Beniash, Samuel I. Stupp, SCIENCE, vol. 294, p. 1684 to 1688 (2001)
[Non-Patent Document 4]
Shinji Matsumoto, Itaru Hamachi, Dojin News, No. 118, p. 1 to 16 (2006)
[Non-Patent Document 5]
Kjeld J. C. Van Bommel et al., Angew. Chem. Int. Ed., vol. 43, p. 1663 to 1667 (2004)

DISCLOSURE OF THE INVENTION

Problems to be Solved by the Invention

In a related-art hydrogel, for forming a synthetic polymer gel of the hydrogel, or depending on the case, for gelling a natural polymer such as a gelatin (collagen), a crosslinker having an aldehyde group is necessary to be used.

In addition, for imparting functions, needless to say to a natural polymer gel, to a (synthetic) polymer gel, a copolymerization reaction is necessary to be effected for chemically modifying a polymer chain or for introducing a functional molecule.

Thus, a related-art hydrogel has such problems that the preparation of the gel is cumbersome and that an unreacted crosslinker or unreacted substances during the copolymerization reaction remain.

In addition, in the case (1.) as described above where the hydrogelators for forming a non-covalent gel which have been disclosed hitherto have the amphipathic low molecular weight molecule as the skeleton, depending on the liquid property of the medium, the gel formation may not be achieved. In other words, in an alkaline range, a reaction mixture forms a micelle to become an emulsified liquid. On the other hand, although in an acidic range, the low molecular weight molecules are self-assembled into a fiber shape and a hydrogel can be obtained, there is disclosed substantially no example in which, in a neutral range regarded as safe for the organism, the hydrogelation is achieved. In addition, the related-art hydrogel also has a problem that the safety of a quaternary ammonium cation (for example, Patent Document 1) and the like for the organism environment is still questioned.

In addition, in the case (2.) where the hydrogelators have a skeleton in the motif of intravital components, the agents have such a problem concerning the productivity that they are not suitable for the mass production and a problem that the gel forming ability depends on a temperature and pH.

Further, in the case (3.) where the hydrogelators have a semi-artificial low molecular weight molecule as the skeleton, for example, referring to a reaction scheme (FIG. 1) for synthesizing a glycoside amino acid derivative constituting the hydrogelator which is described in Patent Document 2, there is specified that sodium azide having high toxicity is used, and further, for self-assembling a hollow fiber described in Patent Document 3, it is essential to add a transition metal (ion). Therefore, these examples leave a problem concerning biocompatibility and the environmental safety.

Thus, further improvements are required for various non-covalent hydrogels and hydrogelators for forming the gels which have been hitherto disclosed in terms of the gel forming ability (gel structure retaining ability), the safety for the organism environment and the like.

Further, from the viewpoint of the safety for the organism environment, there is a potential requirement for a hydrogelator capable of forming a gel with a smaller adding amount.

In order to solve the problems described above, it is an object of the present invention to provide a hydrogelator having high hydrogel-forming ability capable of forming a hydrogel with an extremely small amount thereof over a wide liquid property range from acidic to alkaline, particularly even in a neutral range.

It is another object of the present invention to provide a hydrogel retaining a gel structure stably over a wide liquid property range from acidic to alkaline and having high environmental suitability, biocompatibility and biodegradability.

Means for Solving the Problems

As a result of assiduous research intended to overcome these disadvantages, the present inventors have found the present invention.

That is, according to a first aspect, a hydrogelator is characterized by containing a lipid peptide represented by Formula (1):

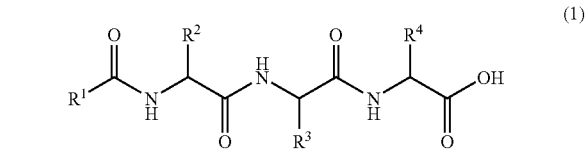

(where $R^1$ represents an aliphatic group having 9 to 21 carbon atoms; $R^2$, $R^3$ and $R^4$ independently represent a hydrogen atom, an alkyl croup having 1 to 4 carbon atom(s) which may have a branched chain having 1 or 2 carbon atom(s), a phenylmethyl group or a —$(CH_2)_n$—X group, and at least one of $R^2$, $R^3$ and $R^4$ represents a —$(CH_2)_n$—X group; n represents the number of 1 to 4; and X represents an amino group, a guanidino group, a —$CONH_2$ group or a 5-membered ring, a 6-membered ring or a fused heterocyclic ring composed of a 5-membered ring and a 6-membered ring which may have 1 to 3 nitrogen atom(s)), or a pharmaceutically usable salt thereof.

According to a second aspect, the hydrogelator according to the first aspect is characterized in that $R^1$ represents a straight chain aliphatic group having 11 to 17 carbon atoms which may have 1 or 2 unsaturated bond(s).

According to a third aspect, the hydrogelator according to the first aspect or the second aspect is characterized in that: $R^2$, $R^3$ and $R^4$ independently represent a hydrogen atom, a methyl group, an ethyl group, an isopropyl group, an isobutyl group, a sec-butyl group, a phenylmethyl group or a —$(CH_2)_n$—X group, and one or two of $R^2$, $R^3$ and $R^4$ represent(s) a —$(CH_2)_n$—X group; n represents the number of 1 to 4; and X represents an amino group, a pyrrolyl group, an imidazolyl group, a pyrazolyl group or an indolyl group.

According to a fourth aspect, the hydrogelator according to the third aspect is characterized in that $R^2$, $R^3$ and $R^4$ independently represent a hydrogen atom, a methyl group, an ethyl group, an isopropyl group, an isobutyl group, a sec-butyl group, a phenylmethyl group, a 2-aminoethyl group, a 4-aminobutyl group, a 4-amino-pyrrolylmethyl group, an imidazolylmethyl group, a pyrazolylmethyl group or a 3-indolylmethyl group, and one or two of $R^2$, $R^3$ and $R^4$ represent(s) a 2-aminoethyl group, a 4-aminobutyl group, a 4-amino-pyrrolylmethyl group, an imidazolylmethyl group, a pyrazolylmethyl group or a 3-indolylmethyl group.

According to a fifth aspect, the hydrogelator according to the fourth aspect is characterized in that $R^2$, $R^3$ and $R^4$ independently represent a hydrogen atom, a methyl group, an isopropyl group, an isobutyl group, a sec-butyl group, a phenylmethyl group, a 4-aminobutyl group, an imidazolylmethyl group or a 3-indolylmethyl group, and one or two of $R^2$, $R^3$ and $R^4$ represent(s) a 4-aminobutyl group, an imidazolylmethyl group or a 3-indolylmethyl group.

According to a sixth aspect, the hydrogelator according to the fifth aspect is characterized in that $R^2$, $R^3$ and $R^4$ independently represent a hydrogen atom, a methyl group, a 4-aminobutyl group or an imidazolylmethyl group, and one or two of $R^2$, $R^3$ and $R^4$ represent(s) a 4-aminobutyl group or an imidazolylmethyl group.

According to a seventh aspect, a fiber is formed by a self-assembly of the hydrogelator as described in any one of the first aspect to the sixth aspect.

According to an eighth aspect, a hydrogel contains the hydrogelator as described in any one of the first aspect to the sixth aspect or the fiber as described in the seventh aspect and an aqueous solution or an alcohol aqueous solution.

Effects of the Invention

The hydrogelator of the present invention can form a hydrogel by gelling an aqueous solution or an alcohol aqueous solution without using a crosslinker or the like required during the formation of a related-art hydrogel, so that there is no unreacted crosslinker remained. In addition, the hydrogelator of the present invention contains low molecular weight compounds, so that the hydrogelator can form a hydrogel without containing unreacted substances of functional molecules introduced into a related-art hydrogelator for developing functions.

In addition, the hydrogelator of the present invention can form a hydrogel over a wide range of liquid properties from an acidic range to an alkaline range. Particularly, from the viewpoint of high safety required for a cell culture base material, medical materials or the like, the hydrogelator of the present invention having a gel forming ability even in a neutral range is useful in the above applications.

In addition, the hydrogelator of the present invention can form a hydrogel only with a small adding amount of 0.1% by mass and applies low load to the environment and the organism when the hydrogelator is taken in.

Further, the hydrogelator of the present invention can form a hydrogel even when a dispersion medium of the hydrogelator contains up to around 50% by volume of an alcohol solvent such as ethanol, so that the hydrogelator of the present invention can be preferably used in hydrogel applications requiring sterilizing properties.

In addition, the hydrogelator of the present invention is a gel-forming agent of artificial low molecular weight molecules which is composed of only lipid and a peptide and uses no animal-derived material (such as collagen, gelatin and matrigel) which is recently leading to a problem of BSE infection or the like, so that the hydrogel obtained from the hydrogelator causes no problem by the infection or the like. Moreover, the hydrogelator having high safety can be produced only by an amidation reaction of lipid and a peptide without using a reagent having a high reactivity but also having toxicity, such as sodium azide.

Here, the lipid peptide constituting the hydrogelator of the present invention can be used as a novel peptide useful in treating the alopecia, applications for treating a photo-damaged skin (for accelerating a synthesis of collagen), UTG inducing factors in cosmetics, chelating agents, medical materials (applications for filling the bone containing calcium phosphate), compositions for lipsticks (for improving the color or the like), as well as applications for cosmetics.

In addition, with respect to the fiber of the present invention, when the hydrogelator is self-assembled, a peptide moiety (amino acid) becomes positioned in the outermost side (that is, the fiber surface), so that when the fiber enters an organism, the fiber is difficult to cause a rejection against organism cells and is excellent in cell-adhesiveness. Therefore, the fiber can be preferably used in a medical sustained-release carrier and an absorbent, a scaffolding for the regeneration medicine and the like.

The fiber is useful as: besides the above applications, a stabilizer, dispersant and humectant in the food industry, agroforestry, cosmetics field and fiber industry; nano-parts in which metals or conductive materials are doped in the electronics and information field; and materials for a filter and conductive materials.

Then, the hydrogel of the present invention can stably retain a gel structure over a wide range of liquid properties from an acidic range to an alkaline range, particularly even under a neutral condition, so that the hydrogel of the present invention is preferred in applications of materials for the biochemistry such as a cell culture and of medical materials.

In addition, the hydrogel of the present invention can be obtained by adding a smaller amount of the hydrogelator than that for a related-art hydrogel as described above, so that it may be said that the hydrogel of the present invention is a hydrogel having high safety both in the organism and in the environment.

Further, the hydrogel of the present invention can stably retain a gel structure even when the dispersion medium of the hydrogel contains up to around 50% by volume of an alcohol solvent such as ethanol, so that the hydrogel of the present invention can be preferably used in applications requiring sterilizing properties.

Further, as described above, when the hydrogel obtained from a hydrogelator which is a lipid peptide-type low molecular weight compound is used in an external environment, for example in the soil, the hydrogel is easily degraded by soil bacteria or the like, or when the hydrogel is used in an organism, the hydrogel is easily degraded by metabolic enzyme, so that the hydrogel applies low load to the environment and the organism.

BEST MODES FOR CARRYING OUT THE INVENTION

Hydrogelator

The hydrogelator of the present invention has a structure represented by Formula (1):

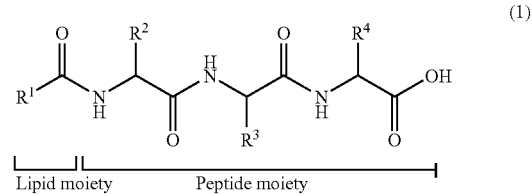

and is composed of a lipid moiety (an alkylcarbonyl group) having a long chain with high lipophilicity and a peptide moiety (tripeptide).

In Formula (1), it is desired that $R^1$ contained in the lipid moiety represents an aliphatic group having 9 to 21 carbon atoms, preferably a straight chain aliphatic group having 11 to 17 carbon atoms which may have one or two unsaturated bond(s).

Particularly preferred specific examples of the structure of the lipid moiety composed of $R^1$ and a carbonyl group adjacent thereto include a lauroyl group, a dodecylcarbonyl group, a myristoyl group, a tetradecylcarbonyl group, a palmitoyl group, a margaroyl group, an oleoyl group, an elaidoyl group, a linoleoyl group, a stearoyl group, and a vaccenoyl group and among them, more preferred are a lauroyl group, a myristoyl group, a palmitoyl group, a margaroyl group, an elaidoyl group and a stearoyl group.

In Formula (1), $R^2$, $R^3$ and $R^4$ contained in the peptide moiety independently represent a hydrogen atom, an alkyl group having 1 to 4 carbon atom(s) which may have a branched chain having 1 or 2 carbon atom(s), a phenylmethyl group or a —$(CH_2)_n$—X group, and at least one, preferably one or two of $R^2$, $R^3$ and $R^4$ represent(s) a —$(CH_2)_n$—X group.

In the —$(CH_2)_n$— group, n represents the number of 1 to 4; and X represents an amino group, a guanidino group, a —$CONH_2$ group or a 5-membered ring, a 6-membered ring or a fused heterocyclic ring composed of a 5-membered ring and a 6-membered ring which may have 1 to 3 nitrogen atom(s).

The alkyl group having 1 to 4 carbon atom(s) which may have a branched chain having 1 or 2 carbon atom(s) represents preferably a methyl group, an ethyl group, an isopropyl group, an isobutyl group, a sec-butyl group, or the like, more preferably a methyl group, an isopropyl group, an isobutyl group or a sec-butyl group, most preferably a methyl group.

In the —$(CH_2)_n$—X group, X represents preferably an amino group, a pyrrolyl group, an imidazolyl group, a pyrazolyl group or an indolyl group.

Accordingly, the —$(CH_2)_n$—X group represents preferably a 2-aminoethyl group, a 4-aminobutyl group, a 4-aminopyrrolylmethyl group, an imidazolylmethyl group, a pyrazolylmethyl group or a 3-indolylmethyl group, more preferably a 4-aminobutyl group, an imidazolylmethyl group or a 3-indolylmethyl group, most preferably a 4-aminobutyl group or an imidazolylmethyl group.

In the compound represented by Formula (1), as a particularly preferred compound, there can be mentioned the compounds formed from the following lipid moieties and peptide moieties (amino acid-assembled portion). Here, the abbreviated names of the amino acids are represented as follows: histidine (His); glycine (Gly); phenylalanine (Phe); valine (Val); isoleucine (Ile); alanine (Ala); leucine (Lue); lysine (Lys); and tryptophan (Trp).

N-lauroyl-Gly-Gly-His, N-lauroyl-Gly-His-Gly, N-lauroyl-His-Gly-Gly, N-lauroyl-Gly-Gly-Lys, N-lauroyl-Gly-Gly-Trp, N-lauroyl-Gly-Ala-His, N-lauroyl-Gly-Val-His, N-lauroyl-Gly-Lue-His, N-lauroyl-Gly-Ile-His, N-lauroyl-Gly-Phe-His, N-lauroyl-Ala-Gly-His, N-myristoyl-Gly-Gly-His, N-myristoyl-Gly-His-Gly, N-myristoyl-His-Gly-Gly, N-myristoyl-Gly-Gly-Lys, N-myristoyl-Gly-Gly-Trp, N-myristoyl-Gly-Ala-His, N-myristoyl-Gly-Val-His, N-myristoyl-Gly-Lue-His, N-myristoyl-Gly-Ile-His, N-myristoyl-Gly-Phe-His, N-myristoyl-Ala-Gly-His, N-palmitoyl-Gly-Gly-His, N-palmitoyl-Gly-His-Gly, N-palmitoyl-His-Gly-Gly, N-palmitoyl-Gly-Gly-Lys, N-palmitoyl-Gly-Gly-Trp, N-palmitoyl-Gly-Ala-His, N-palmitoyl-Gly-Val-His, N-palmitoyl-Gly-Lue-His, N-palmitoyl-Gly-Ile-His, N-palmitoyl-Gly-Phe-His, N-palmitoyl-Ala-Gly-His, N-margaroyl-Gly-Gly-His, N-margaroyl-Gly-His-Gly, N-margaroyl-His-Gly-Gly, N-margaroyl-Gly-Gly-Lys, N-margaroyl-Gly-Gly-Trp, N-margaroyl-Gly-Ala-His, N-margaroyl-Gly-Val-His, N-margaroyl-Gly-Lue-His, N-margaroyl-Gly-Ile-His, N-margaroyl-Gly-Phe-His, N-margaroyl-Ala-Gly-His, N-stearoyl-Gly-Gly-His, N-stearoyl-Gly-His-Gly, N-stearoyl-His-Gly-Gly, N-stearoyl-Gly-Gly-Lys, N-stearoyl-Gly-Gly-Trp, N-stearoyl-Gly-Ala-His, N-stearoyl-Gly-Val-His, N-stearoyl-Gly-Lue-His, N-stearoyl-Gly-Ile-His, N-stearoyl-Gly-Phe-His, N-stearoyl-Ala-Gly-His, N-elaidoyl-Gly-Gly-His, N-elaidoyl-Gly-His-Gly, N-elaidoyl-His-Gly-Gly, N-elaidoyl-Gly-Gly-Lys, N-elaidoyl-Gly-Gly-Trp, N-elaidoyl-Gly-Ala-His, N-elaidoyl-Gly-Val-His, N-elaidoyl-Gly-Lue-His, N-elaidoyl-Gly-Ile-His, N-elaidoyl-Gly-Phe-His, N-elaidoyl-Ala-Gly-His, N-arachidoyl-Gly-Gly-His, N-arachidoyl-Gly-His-Gly, N-arachidoyl-His-Gly-Gly, N-arachidoyl-Gly-Gly-Lys, N-arachidoyl-Gly-Gly-Trp, N-arachidoyl-Gly-Ala-His, N-arachidoyl-Gly-Val-His, N-arachidoyl-Gly-Lue-His, N-arachidoyl-Gly-Ile-His, N-arachidoyl-Gly-Phe-His, N-arachidoyl-Ala-Gly-His, N-behenoyl-Gly-Gly-His, N-behenoyl-Gly-His-Gly, N-behenoyl-His-Gly-Gly, N-behenoyl-Gly-Gly-Lys, N-behenoyl-Gly-Gly-Trp, N-behenoyl-Gly-Ala-His, N-behenoyl-Gly-Val-His, N-behenoyl-Gly-Lue-His, N-behenoyl-Gly-Ile-His, N-behenoyl-Gly-Phe-His, and N-behenoyl-Ala-Gly-His.

Among the above compounds, examples of a more preferred lipid peptide compound include N-lauroyl-Gly-Gly-His, N-lauroyl-Gly-His-Gly, N-lauroyl-His-Gly-Gly, N-lauroyl-Gly-Gly-Lys, N-lauroyl-Gly-Gly-Trp, N-lauroyl-Gly-Ala-His, N-lauroyl-Gly-Val-His, N-lauroyl-Gly-Lue-His, N-lauroyl-Gly-Ile-His, N-lauroyl-Gly-Phe-His, N-myristoyl-Gly-Gly-His, N-myristoyl-Gly-His-Gly, N-myristoyl-His-Gly-Gly, N-myristoyl-Gly-Gly-Lys, N-myristoyl-Gly-Gly-Trp, N-myristoyl-Gly-Ala-His, N-myristoyl-Gly-Val-His, N-myristoyl-Gly-Lue-His, N-myristoyl-Gly-Ile-His, N-myristoyl-Gly-Phe-His, N-palmitoyl-Gly-Gly-His, N-palmitoyl-Gly-His-Gly, N-palmitoyl-His-Gly-Gly, N-palmitoyl-Gly-Gly-Lys, N-palmitoyl-Gly-Gly-Trp, N-palmitoyl-Gly-Ala-His, N-palmitoyl-Gly-Val-His, N-palmitoyl-Gly-Lue-His, N-palmitoyl-Gly-Ile-His, N-palmitoyl-Gly-Phe-His, N-palmitoyl-Ala-Gly-His, N-margaroyl-Gly-Gly-His, N-margaroyl-Gly-His-Gly, N-margaroyl-His-Gly-Gly, N-margaroyl-Gly-Gly-Lys, N-margaroyl-Gly-Gly-Trp, N-margaroyl-Gly-Ala-His, N-margaroyl-Gly-Val-His, N-margaroyl-Gly-Lue-His, N-margaroyl-Gly-Ile-His, N-margaroyl-Gly-Phe-His, N-stearoyl-Gly-Gly-His, N-stearoyl-Gly-His-Gly, N-stearoyl-His-Gly-Gly, N-stearoyl-Gly-Gly-Lys, N-stearoyl-Gly-Gly-Trp, N-stearoyl-Gly-Ala-His, N-stearoyl-Gly-Val-His, N-stearoyl-Gly-Lue-His, N-stearoyl-Gly-Ile-His, N-stearoyl-Gly-Phe-His, N-elaidoyl-Gly-Gly-His, N-elaidoyl-Gly-His-Gly, N-elaidoyl-His-Gly-Gly, N-elaidoyl-Gly-Gly-Lys, N-elaidoyl-Gly-Gly-Trp, N-elaidoyl-Gly-Ala-His, N-elaidoyl-Gly-Val-His, N-elaidoyl-Gly-Lue-His, N-elaidoyl-Gly-Ile-His, N-elaidoyl-Gly-Phe-His, N-arachidoyl-Gly-Gly-His, N-arachidoyl-Gly-His-Gly, N-arachidoyl-His-Gly-Gly, N-arachidoyl-Gly-Gly-Lys, N-arachidoyl-Gly-Gly-Trp, N-arachidoyl-Gly-Ala-His, N-arachidoyl-Gly-Val-His, N-arachidoyl-Gly-Lue-His, N-arachidoyl-Gly-Ile-His, N-arachidoyl-Gly-Phe-His, N-behenoyl-Gly-Gly-His, N-behenoyl-Gly-His-Gly, N-behenoyl-His-Gly-Gly, N-behenoyl-Gly-Gly-Lys, N-behenoyl-Gly-Gly-Trp, N-behenoyl-Gly-Ala-His, N-behenoyl-Gly-Val-His, N-behenoyl-Gly-Lue-His, N-behenoyl-Gly-Ile-His, and N-behenoyl-Gly-Phe-His, and examples of the most preferred compound include N-palmitoyl-Gly-Gly-His, N-palmitoyl-Gly-His-Gly, N-palmitoyl-His-Gly-Gly, N-palmitoyl-Gly-Gly-Lys, N-palmitoyl-Gly-Gly-Phe and N-lauroyl-Gly-Gly-His.

(Fiber Formed from Hydrogelator)

When the hydrogelator of the present invention is charged into an aqueous solution or an alcohol aqueous solution, the peptide moiety in Formula (1) forms an intermolecular non-covalent bond through a hydrogen bond and on the other hand, the lipid moiety in Formula (1) is self-assembled so as to be hydrophobically packed to form a cylindrical secondary assembly, that is, a fiber.

For reference, in FIG. 1, there is shown one example of the conceptual diagram of the self-assembly and gelation of the lipid peptide constituting the hydrogelator of the present invention. Molecules of the lipid peptide (a) are assembled with a central focus on the lipid moiety which is a hydrophobic site (b) to form a fiber (c) by the self-assembly.

(Hydrogel)

When the fiber is formed in an aqueous solution or an alcohol aqueous solution, the fiber forms a three-dimensional network structure (for example, refer to (d) in FIG. 1) and further, a non-covalent bond is formed between the hydrophilic portion (peptide moiety) in the fiber surface and an aqueous solvent, and the fiber swells, so that the whole aqueous solution or alcohol aqueous solution is gelled to form a hydrogel.

Although the detail of a detailed mechanism during the formation of the hydrogel of the present invention has been not yet elucidated, it is estimated that the charge state of the hydrogelator molecule is involved therein.

The hydrogelator of the present invention is an ampholytic compound having a carboxyl group at a C terminal and an amino group derived from a side chain —$(CH_2)_n$—X group in the peptide moiety. It is considered that the ion state of the hydrogelator is in an equilibrium among such four states as a state in which only a carboxyl group is anionized, a state in which only an amino group is cationized, a state in which the hydrogelator is ampho-ionized and a state in which both substituents are not ionized.

Taking into consideration the acid dissociation constant of an amino acid residue, it is considered that the following states exist frequently: in the hydrogelator molecule, a terminal amino group derived from a —$(CH_2)_n$—X group in the peptide moiety is positively charged to be cationized in an acidic range; a terminal carboxyl group at a C terminal of the peptide moiety is negatively charged to be anionized in a basic range; and the hydrogelator molecule is ampho-ionized in a neutral range.

When the hydrogelator is ionized, the affinity of the peptide moiety with water is enhanced and the hydrogelator is self-assembled so that a long chain portion which is the hydrophobic portion is distanced from the contact with water to form a nanofiber. At this time, when an ampho-ion state exists dominantly, ion bonds of cations and anions are formed between nanofibers to form a network structure forming a crosslinkage structure. It is considered that by the formation of this network structure, the nanofiber becomes possible to incorporate a larger amount of water, so that excellent hydrogel forming ability is developed.

As described above, the hydrogelator of the present invention can form a stable hydrogel even in a neutral range. In addition, since the lipid peptide-type hydrogelator of the present invention is a low molecular weight compound, both of the hydrogelator and the hydrogel obtained therefrom are degradable in the environment and the organism, and a hydrogelator and a hydrogel having high biocompatibility can be obtained.

Therefore, the hydrogelator and the hydrogel obtained therefrom of the present invention can be used in materials for various fields such as cell culture base materials, preservation materials for organism molecules such as cells and proteins, base materials for external use, materials for medical use, materials for biochemistry, cosmetics materials, food materials, contact lenses, paper diapers, artificial actuators, and materials for dry-land agriculture. In addition, as a bioreactor carrier such as enzymes, the hydrogelator and the hydrogel obtained therefrom can be widely utilized in studies, medicines, analyses and various industries.

Moreover, since the hydrogel of the present invention is a gel formed from a low molecular weight compound, by a design of the compound, various functions, for example, capable of forming a gel performing a sol-gel conversion by responding to an external stimulation, can be easily imparted to the hydrogel without a necessity of modifying a polymer chain or effecting a copolymerization reaction.

EXAMPLES

Hereinafter, the present invention will be further described in more detail referring to Examples, which should not be construed as limiting the scope of the present invention.

Abbreviations Used in Examples

The meanings of abbreviations used in Examples are as follows.
Gly: glycine
His: histidine
Lys: lysine
Phe: phenylalanine
HBTU: 2-(1H-benzotriazole-1-yl)-1,1,3,3-tetramethyluronium-hexafluorophosphate (manufactured by Watanabe. Chemical Industries, Ltd.)
HOBt: 1-hydroxy-benzotriazole (manufactured by Wako Pure Chemical Industries, Ltd.)
DMF: dimethylformamide
DCM: dichloromethane
DIEA: N,N-diisopropylethylamine (manufactured by Tokyo Chemical Industry Co., Ltd.)
TFA: trifluoroacetic acid (manufactured by Watanabe Chemical Industries, Ltd.)
TIS: triisopropylsilane (manufactured by Watanabe Chemical Industries, Ltd.)

(Synthesis of Lipid Peptide)

The lipid peptide was synthesized according to the following procedure of an Fmoc solid phase peptide synthesis method. As the resin, mainly used was an amino acid-Barlos Resin. The synthesis was performed under a synthesis scale of 0.3 mmol.

Example 1

Synthesis of N-palmitoyl-Gly-Gly-His

About 390 mg of His-Barlos Resin (manufactured by Watanabe Chemical Industries, Ltd.) was charged into a PD-10 column and was washed with 5 mL of DCM three times, and next with 5 mL of DMF three times.

Next, into the column, about 270 mg of Fmoc-Gly-OH (manufactured by Watanabe Chemical Industries, Ltd.) and 2.1 mL of a condensing agent solution 1 (in which 3.05 g of HBTU and 1.25 g of HOBt were dissolved in 16 mL of DMF) were charged.

Further, 2.1 mL of a condensing agent solution 2 (in which 2.75 mL of DIEA was dissolved in 14.25 mL of DMF) was charged into the column.

The content of the column was stirred using a vibrator for 30 minutes and then was washed with 5 mL of DMF five times, next with 5 mL of DCM three times and further with 5 mL of DMF three times.

Next, 5 mL of a 20% piperidine/DMF solution was added to the reaction Mixture. The resultant mixture was stirred for 1 minute and then, the solution was removed. Subsequently, 5 mL of a 20% piperidine/DMF solution was added again to the reaction mixture. The resultant mixture was stirred for 45 minutes and washed with 5 mL of DMF five times.

Further, 270 mg of Fmoc-Gly-OH and each 2.1 mL of the condensing agent solution 1 and the condensing agent solution 2 were added to the reaction mixture. The resultant mixture was stirred using a vibrator for 20 minutes and then, was washed with 5 mL of DMF five times, next with 5 mL of DCM three times and further with 5 mL of DMF three times.

Next, 5 mL of a 20% piperidine/DMF solution was added to the reaction mixture. The resultant mixture was stirred for 1 minute and then, the solution was removed. Subsequently, 5 mL of a 20% piperidine/DMF solution was added again to the reaction mixture. The resultant mixture was stirred for 45 minutes and was washed with 5 mL of DMF five times.

About 230 mg of palmitic acid (manufactured by Tokyo Chemical Industry Co., Ltd.) was charged into the column and thereto, each 2.1 mL of the condensing agent solution 1 and the condensing agent solution 2 were added, followed by stirring the reaction mixture using a vibrator for 90 minutes.

After the completion of the reaction, the reaction mixture was washed with 5 mL of DMF five times, next with 5 mL of DCM five times and further with 5 mL of methanol five times and then the resin was lyophilized over one night.

After the drying, 3.8 mL of TFA and 0.1 mL of TIS were charged into the column and the content of the column was stirred for 1 hour.

To the recovered mixed solution, water was added so that a solid was deposited and then the product was recovered by suction filtration. The product was freeze-dried and then was washed with 4 mL of acetonitrile three times to obtain the objective compound.

FT-MS$^+$ m/z calc. for C26H46N5O5 (M+H)$^+$ 507. 34207. Found 507. 92

Example 2

Synthesis of N-palmitoyl-Gly-His-Gly

According to substantially the same procedure as in Example 1, that is, by loading 342 mg of Fmoc-Gly Resin (manufactured by Watanabe Chemical Industries, Ltd.) in a column, by condensing 620 mg of Fmoc-His(Trt)-OH (manufactured by Watanabe Chemical Industries, Ltd.) and 293 mg of Fmoc-Gly-OH in this order to the Resin by an Fmoc method, and finally by reacting 321 mg of palmitic acid, 53.3 mg of the objective compound was obtained.

$^1$H-NMR (500 MHz DMSO-d$_6$ δ ppm): 8.56 (1H, s, C-2 His), 8.33 (1H, t, 3J=5.8 Hz, NH Gly), 8.14 (1H, d, 3J=8.3 μL, NH His), 8.06 (1H, t, 3J=5.8 Hz, NH Gly), 7.19 (1H, s, C-4 His), 4.57 (1H, m, α-CH His), 3.82-3.67 (4H, m, α-CH Gly), 3.07 (1H, m, β-CH2a His), 2.90 (1H, m, β-CH2b His), 2.11 (2H, t, J=7.5 Hz, CH2 Pal), 1.48-1.45 (2H, m, CH2 Pal), 1.23 (24H, brs, CH2 Pal), 0.85 (3H, t, J=6.9 Hz, CH3 Pal);

FT-MS$^+$ m/z calc. for C26H46N5O5 (M+H)$^+$ 508. 34990. Found 508. 34778

Example 3

Synthesis of N-palmitoyl-His-Gly-Gly

According to substantially the same procedure as in Example 1, that is, by loading 171 mg of Fmoc-Gly Resin in a column, by condensing 149 mg of Fmoc-Gly-OH and 310 mg of Fmoc-His(Trt)-OH in this order to the Resin by an Fmoc method, and finally by reacting 160 mg of palmitic acid, 27.8 mg of the objective compound was obtained.

$^1$H-NMR (500 MHz DMSO-d$_6$ δ ppm): 8.53 (1H, brs, C-2 His), 8.38 (1H, t, 3J=5.5 Hz, NH Gly), 8.26 (1H, t, 33=5.8 Hz, NH Gly), 8.04 (1H, d, 33=8.0 Hz, NH His), 7.20 (1H, s, C-4 His), 4.55 (1H, m, α-CH His), 3.82-3.68 (4H, m, α-CH Gly), 3.04 (1H, m, β-CH2a His), 2.88 (1H, m, β-CH2b His), 2.09 (2H, t, J=7.5 Hz, CH2 Pal), 1.44-1.39 (2H, m, CH2 Pal), 1.24 (24H, brs, CH2 Pal), 0.85 (3H, t, J=7.0 Hz, CH3 Pal);

FT-MS$^+$ m/z calc. for C26H46N5O5 (M+H)$^+$ 508. 34990. Found 508. 34763

Example 4

Synthesis of N-palmitoyl-Gly-Gly-Lys

According to substantially the same procedure as in Example 1, that is, by loading 394.7 mg of Lys(Boc)-Trt(2-Cl) Resin (manufactured by Watanabe Chemical Industries, Ltd.) in a column, by condensing 270 mg of Fmoc-Gly-OH and further 270 mg of Fmoc-Gly-OH in this order to the Resin by an Fmoc method, and finally by reacting 230 mg of palmitic acid, the objective compound was obtained.

FT-MS$^+$ m/z calc. for C28H49N6O6 (M+H)$^+$ 499. 38595. Found 499. 3578

Example 5

Synthesis of N-palmitoyl-Gly-Gly-Phe

According to substantially the same procedure as in Example 1, that is, by loading 576.9 mg of Phe(Boc)-Trt(2-Cl) Resin (manufactured by Watanabe Chemical Industries, Ltd.) in a column, by condensing 270 mg of Fmoc-Gly-OH and further 270 mg of Fmoc-Gly-OH in this order to the Resin by an Fmoc method, and finally by reacting 230 mg of palmitic acid, the objective compound was obtained.

Example 6

Synthesis of N-Lauroyl-Gly-Gly-His

According to substantially the same procedure as in Example 1, that is, by loading 390 mg of His-Barlos Resin in a column, by condensing 270 mg of Fmoc-Gly-OH and further 270 mg of Fmoc-Gly-OH in this order to the Resin by an Fmoc method, and finally by reacting 180 mg of lauric acid, the objective compound was obtained.

(Evaluation of Hydrogelation of Lipid Peptide with Pure Water)

A lipid peptide synthesized in Example 3 was charged into a sample tube and pure water (prepared by converting water into an ultrapure water using Milli-Q system (manufactured by Nihon Millipore K.K.)) was added to the sample tube so that the concentration of the lipid peptide in the aqueous solution becomes 0.5 or 0.1% by mass, followed by heating the content of the sample tube to 90° C. or more to dissolve the lipid peptide and then by leaving the resultant solution to cool down.

A state in which after leaving the resultant solution to cool down, the fluidity of the solution was lost and when the sample tube was inverted, the solution did not flow down, was evaluated as "gelled (☒)" and pH value of the solution at room temperature was measured.

TABLE 1

Evaluation of hydrogelation of lipid peptide by pure water

|  | | 0.5% (w/v) | | 0.1% (w/v) | |
| --- | --- | --- | --- | --- | --- |
|  | | Gelled | pH | Gelled | pH |
| Example 3 | N-palmitoyl-His-Gly-Gly | ○ | 7.0 | ○ | 7.4 |

(Evaluation of Hydrogelation of Lipid Peptide, by Acidic Buffer Solution)

Lipid peptides synthesized in Examples 1 to 3 were charged into sample tubes and a phosphate buffer solution (PBS) (pH=2.0) was added to each of the sample tubes so that the concentration of the lipid peptide in the aqueous solution becomes 0.5 or 0.1% by mass. Subsequently, the content of the sample tube was heated to 90° C. or more to dissolve the lipid peptide, followed by leaving the resultant solution to cool down.

A state in which after leaving the resultant solution to cool down, the fluidity of the solution was lost and when the sample tube was inverted, the solution did not flow down, was evaluated as "gelled (○)" and pH value of the solution at room temperature was measured.

TABLE 2

Evaluation of hydrogelation of lipid peptide by acidic buffer solution

|  | | 0.5% (w/v) | | 0.1% (w/v) | |
| --- | --- | --- | --- | --- | --- |
|  | | Gelled | pH | Gelled | pH |
| Example 1 | N-palmitoyl-Gly-Gly-His | ○ | — | ○ | — |
| Example 2 | N-palmitoyl-Gly-His-Gly | ○ | 1.8 | ○ | 1.9 |
| Example 3 | N-palmitoyl-His-Gly-Gly | ○ | 1.8 | ○ | 1.9 |

(Evaluation of Hydrogelation of Lipid Peptide by Neutral Buffer Solution)

A lipid peptide synthesized in Example 3 was charged into a sample tube and a phosphate buffer solution (PBS) (pH=7.5) was added to the sample tube so that the concentration of the lipid peptide in the aqueous solution becomes 0.5 or 0.1% by mass. Subsequently, the content of the sample tube was heated to 90° C. or more to dissolve the lipid peptide, followed by leaving the resultant solution to cool down.

A state in which after leaving the resultant solution to cool down, the fluidity of the solution was lost and when the sample tube was inverted, the solution did not flow down, was evaluated as "gelled (○)" and pH value of the solution at room temperature was measured.

TABLE 3

Evaluation of hydrogelation of lipid peptide by neutral buffer solution

|  | | 0.5% (w/v) | | 0.1% (w/v) | |
| --- | --- | --- | --- | --- | --- |
|  | | Gelled | pH | Gelled | pH |
| Example 3 | N-palmitoyl-His-Gly-Gly | ○ | 7.4 | ○ | 7.3 |

As described above, the lipid peptide (N-palmitoyl-His-Gly-Gly) synthesized in Example 3 was gelled in any of pure water, the acidic buffer solution and the neutral buffer solution only at a concentration of 0.1% by mass.

In addition, also the lipid peptide (N-palmitoyl-Gly-Gly-His) synthesized in Example 1 and the lipid peptide (N-palmitoyl-Gly-His-Gly) synthesized in Example 2 were gelled in the acidic buffer solution at a concentration of 0.1% by mass.

INDUSTRIAL APPLICABILITY

The hydrogelator and the hydrogel obtained therefrom according to the present invention can stably retain a gel structure over a wide liquid property range ranging from an acidic range to an alkaline range, particularly even under a neutral condition, and have extremely high biocompatibility, so that the hydrogelator and the hydrogel are preferred in applications of various functional materials.

For example, from the viewpoint of suitability for the above wide liquid property range, the hydrogelator and the hydrogel are preferred in applications such as cleaning agents (for medical, living, and industrial applications and the like), sol-forming and gel-forming agents (applications for cosmetics and other products for daily use), a gel-forming agent for a dye stabilizing application, and food additives (for acidic food, alkaline food, neutral food, and the like).

In addition, the hydrogelator and the hydrogel can be applied in a neutral range, as materials for biology and biochemistry such as cell culture basic materials and skin basic materials, and in an acidic range, as basic materials of pharmaceutical preparations such as gastric acid adjusters, enteric coated preparations and biodegradable anti-metabolic agents by the feeling of fullness, as stabilizers and additives during the production of acidic milk beverages containing pectin, etc., or in applications for improving an alkaline soil, or the like.

Further, in an alkaline range, the hydrogelator and the hydrogel can be used as stabilizers and additives during the production of alkaline beverages and milk beverages, as applications for catalytic reactions using various alkaline enzymes (alkaline protease, alkaline cerase, alkaline amylase, alkaline xylase, alkaline pectate lyase and the like), in industrial applications of alkalophilic bacteria, as gel-forming agents used in alkaline cells and the like, as acidic soil ameliorant applications, as basic materials, reaction additives and accelerators in various industrial applications such as bioreactors, cleaning agents and soaps, cosmetics, drug discoveries, and analytic investigations.

BRIEF DESCRIPTION OF THE DRAWINGS

FIG. 1 is a schematic view showing a conceptual diagram of a self-assembly and gelation following thereto of a hydrogelator molecule.

The invention claimed is:

1. A hydrogelator comprising a lipid peptide represented by Formula (1):

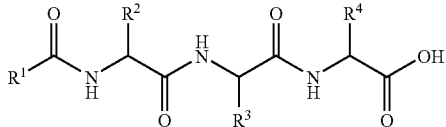

where:
- $R^1$ represents an aliphatic group having 9 to 21 carbon atoms;
- $R^2$, $R^3$ and $R^4$ independently represent a hydrogen atom, an alkyl group having 1 to 4 carbon atom(s) which may have a branched chain having 1 or 2 carbon atom(s), a phenylmethyl group or a —$(CH_2)_n$—X group, and at least one of $R^2$, $R^3$ and $R^4$ represents a —$(CH_2)_n$—X group;
- n represents the number of 1 to 4; and
- X represents an:
  - a —$CONH_2$ group, or
  - a 5-membered ring, a 6-membered ring, or a fused heterocyclic ring composed of a 5-membered ring and a 6-membered ring, which may have 1 to 3 nitrogen atoms; or
- a pharmaceutically acceptable salt thereof.

2. The hydrogelator according to claim 1, wherein $R^1$ represents a straight chain aliphatic group having 11 to 17 carbon atoms which may have 1 or 2 unsaturated bond(s).

3. The hydrogelator according to claim 1, wherein:
$R^2$, $R^3$ and $R^4$ independently represent a hydrogen atom, a methyl group, an ethyl group, an isopropyl group, an isobutyl group, a sec-butyl group, a phenylmethyl group or a —$(CH_2)_n$—X group, and one or two of $R^2$, $R^3$ and $R^4$ represent(s) a —$(CH_2)_n$—X group;
n represents the number of 1 to 4; and
X represents a pyrrolyl group, an imidazolyl group, a pyrazolyl group, or an indolyl group.

4. The hydrogelator according to claim 3, wherein $R^2$, $R^3$ and $R^4$ independently represent a hydrogen atom, a methyl group, an ethyl group, an isopropyl group, an isobutyl group, a sec-butyl group, a phenylmethyl group, a 2-aminoethyl group, a 4-aminobutyl group, a 4-amino-pyrrolylmethyl group, an imidazolylmethyl group, a pyrazolylmethyl group or a 3-indolylmethyl group, and one or two of $R^2$, $R^3$ and $R^4$ represent(s) a 2-aminoethyl group, a 4-aminobutyl group, a 4-amino-pyrrolylmethyl group, an imidazolylmethyl group, a pyrazolylmethyl group or a 3-indolylmethyl group.

5. The hydrogelator according to claim 4, wherein $R^2$, $R^3$ and $R^4$ independently represent a hydrogen atom, a methyl group, an isopropyl group, an isobutyl group, a sec-butyl group, a phenylmethyl group, a 4-aminobutyl group, an imidazolyl methyl group or a 3-indolylmethyl group, and one or two of $R^2$, $R^3$ and $R^4$ represent(s) a 4-aminobutyl group, an imidazolylmethyl group or a 3-indolylmethyl group.

6. The hydrogelator according to claim 5, wherein $R^2$, $R^3$ and $R^4$ independently represent a hydrogen atom, a methyl group, a 4-aminobutyl group or an imidazolylmethyl group, and one or two of $R^2$, $R^3$ and $R^4$ represent(s) a 4-aminobutyl group or an imidazolylmethyl group.

7. A fiber formed by a self-assembly of the hydrogelator as claimed in claim 1.

8. A hydrogel comprising:
the fiber as claimed in claim 7; and
an aqueous solution or an alcohol aqueous solution.

* * * * *